United States Patent
Matsumoto et al.

(10) Patent No.: US 7,408,647 B2
(45) Date of Patent: Aug. 5, 2008

(54) SURFACE PLASMON RESONANCE SENSOR DEVICE

(75) Inventors: Takahiro Matsumoto, Tokyo (JP); Makoto Tomita, Shizuoka (JP)

(73) Assignee: Stanley Electric Co., Ltd., Tokyo (JP)

( * ) Notice: Subject to any disclaimer, the term of this patent is extended or adjusted under 35 U.S.C. 154(b) by 0 days.

(21) Appl. No.: 11/610,854

(22) Filed: Dec. 14, 2006

(65) Prior Publication Data

US 2007/0139654 A1    Jun. 21, 2007

(30) Foreign Application Priority Data

Dec. 19, 2005  (JP) ............................. 2005-365152
Dec. 20, 2005  (JP) ............................. 2005-367182

(51) Int. Cl.
*G01N 21/00* (2006.01)

(52) U.S. Cl. ...................................... 356/445

(58) Field of Classification Search ........................ None
See application file for complete search history.

(56) References Cited

U.S. PATENT DOCUMENTS 5,835,645 A * 11/1998 Jorgenson et al. ............. 385/12
5,858,799 A *  1/1999 Yee et al. ..................... 436/164

FOREIGN PATENT DOCUMENTS

JP    2001-165852    6/2001

* cited by examiner

*Primary Examiner*—Michael P Stafira
(74) *Attorney, Agent, or Firm*—Rankin, Hill & Clark LLP (57) ABSTRACT

Provided is a surface plasmon resonance sensor device having excellent measurement accuracy. The device is equipped with an optical fiber 2,32 for introducing a light incident from one end thereof to the other end, a core exposed portion 3,33a formed to expose core 5,33 of the optical fiber 2,32, and a thin metal film 4,35 formed on the core exposed portion 3,33a and capable of exciting surface plasmon. The core exposed portion 3 is a first microsphere 3 disposed at the other end portion of the optical fiber 2 and the thin metal film 4 is formed on the surface of the microsphere 3. The thin metal film may be a first fine-metal-particle thin film 25 in which fine metal particles 24 have been distributed uniformly. The core exposed portion 33a is disposed in the midway of the optical fiber 32 and the thin metal film 35 is formed to cover therewith the entire surface of the core exposed portion 33a. The core exposed portion 33a is equipped with a second microsphere 36 formed integral with the core 33 and the thin metal film 35 is formed to cover the microsphere 36. The thin metal film 35 may be a second fine-metal-particle thin film 38 in which fine metal particles 37 have been distributed uniformly.

14 Claims, 11 Drawing Sheets

SURFACE PLASMON RESONANCE SENSOR DEVICE

BACKGROUND OF THE INVENTION

1. Field of the Invention

The present invention relates to a surface plasmon resonance sensor device to be used for, for example, biosensors, optical sensors, gas sensors, concentration sensors, and ion sensors.

2. Description of the Related Art

Various sensors making use of surface plasmon resonance such as biosensors, optical sensors, gas sensors, concentration sensors and ion sensors have been proposed in recent years.

Surface plasmon resonance is a phenomenon in which—when a thin metal film having a nanometer order thickness and formed over one surface of a glass prism is exposed to an incident light from the reverse side of the thin metal film under total reflection conditions—an evanescent wave generated along the surface of the thin metal film reaches the opposite side of the thin metal film and resonantly excites surface plasmon which has a wave number equal to that of the evanescent wave. The thin metal film may be a fine-metal-particle thin film composed of fine metal particles distributed uniformly at regular intervals. In this case, surface plasmon resonantly excited on the surface of fine metal particles is sometimes called "localized surface plasmon".

The wave number of the evanescent wave varies, depending on an incident angle of the incident light so that resonance excitation of the surface plasmon can be forced on the opposite side of the thin metal film by controlling the incident angle. The incident light, on the other hand, decreases its intensity (decrease in reflectance) because it consumes its energy when the evanescent wave causes resonance excitation of the surface plasmon. The angle at which the maximum decrease in intensity occurs is called "resonance angle" and it has a direct relation with the wave number of the surface plasmon. The wave number of the surface plasmon which is resonantly excited changes depending on the properties of the surface of the thin metal film on which the surface plasmon is excited.

It therefore becomes possible to detect properties, changes or the like of a substance on the surface of the thin metal film by determining the resonance angle from the angular distribution of the reflected light intensity and grasping a change in the resonance angle. It is also possible to detect the properties, change or the like of a substance on the surface of the thin metal film by grasping a change in the absorption spectrum or reflection intensity of a reflected light instead of a change in the resonance angle. The above-described various sensors can be manufactured by applying thereto the above-described principle.

As sensors utilizing surface plasmon resonance, those obtained by sharpening a tip portion of a light guiding core of an optical fiber in a light guiding direction and forming a thin metal film at the tip portion thus sharpened are conventionally known (refer to, for example, Japanese Patent Laid-Open No. 2001-165852).

In the above-described sensor, a predetermined light incident angle necessary for the surface plasmon resonance is set between a measuring plane, which has been obtained by sharpening the tip portion of a light guiding core of an optical fiber in a light guiding direction, and a light guiding direction by the light guiding core. In this sensor, when a light beam such as laser light irradiated from a light source is guided by the optical fiber to the measuring plane at the sharpened tip portion of the optical fiber, the incident light is reflected, depending on a substance to be measured. The properties, changes or the like of the substance are measured by detecting a change in the intensity of the light reflected depending on the substance to be measured.

The above-described method of grasping a change in the resonance angle and thereby measuring the properties, changes or the like of a substance requires a change in the angle of the incident light so that the apparatus used therefor becomes large and expensive. When the above-described sensor using the sharpened tip portion of a light guiding core of an optical fiber as a measuring plane is employed, on the other hand, an apparatus used therefor can be simplified because an incident light is guided to the measuring plane via the light conducting core and at the same time, a change in the intensity of a light reflected from the measuring plane may be detected by introducing the reflected light into a detector via the light conducting core.

The conventional sensors have however the inconvenience that since the tip portion of a light guiding core of an optical fiber sharpened along the light guiding direction is used as a measuring plane, an area effective for the measurement is limited, leading to difficulty in attaining sufficient measurement accuracy.

SUMMARY OF THE INVENTION

An object of the present invention is to overcome the above-described inconvenience and provide a surface plasmon resonance sensor device having excellent measurement accuracy.

The above-described object can be achieved by a surface plasmon resonance sensor device of the present invention which comprises an optical fiber for introducing a light incident from one end thereof to the other end, a core exposed portion formed to expose the core of the optical fiber, and a thin metal film formed on the core exposed portion and capable of exciting surface plasmon. A quartz fiber or plastic fiber is usable as the optical fiber.

The core exposed portion in the surface plasmon resonance sensor device according to the first aspect of the present invention is a first microsphere which is disposed at the other end portion of the optical fiber and resonates a guided light confined in the microsphere. The thin metal film has been formed on the surface of the first microsphere.

In the surface plasmon resonance sensor device according to the first aspect, a light incident from one end of the optical fiber is guided by the optical fiber to the first microsphere and is resonated by repeated rotation while being confined in the first microsphere. When the incident light is rotated in the first microsphere, an evanescent wave occurs along the surface of the first microsphere and this evanescent wave causes resonance excitation of surface plasmon on the outer surface of the thin metal film.

The incident light rotates, for example, at about $10^9$ times/ms for from 1 to 10 ms along the inner surface of the first microsphere. As a result, an area effective for the measurement of the properties, changes or the like of the substance increases in proportion to the rotation number of the incident light inside the first microsphere, and becomes $10^9$ to $10^{10}$ times as much as that of the actual surface area of the first microsphere, leading to a marked improvement in the measurement accuracy. According to the surface plasmon resonance sensor device of the first aspect, an area effective for measurement increases, whereby excellent measurement accuracy can be attained.

The thin metal film is preferably composed of a first covering layer formed to cover the entire surface of the first microsphere and having a thickness within a range of from 10 to 100 nm. When the thin metal film has a thickness less than 10 nm, a uniform covering layer can hardly be formed. When the thickness of the thin metal film exceeds 100 nm, on the other hand, an evanescent wave hardly penetrates through the covering layer, making it difficult to cause resonance excitation of surface plasmon.

The first covering layer can be composed of at least one metal selected from a group consisting of gold, silver, copper and aluminum.

The thin metal film is more preferably composed of a first fine-metal-particle thin film in which fine metal particles having an average particle size of 50 nm or less have been distributed uniformly at intervals within a range of from 10 to 100 nm. When the thin metal film is the first thin fine-metal-particle film, an area effective for the measurement of the properties, changes or the like of the substance can be increased over that of the first covering layer and the measurement accuracy can be greatly improved further.

When the first fine-metal-particle thin film is used, localized surface plasmon resonance occurs owing to a similar principle to that of the above-described surface plasmon resonance. Occurrence of the localized surface plasmon resonance is presumed to be suppressed when the average particle size of the fine metal particles exceeds 50 nm. When the fine metal particles are arranged at intervals less than 10 nm, fine metal particles having an average particle size of 50 nm or less cannot be formed independently. When they are distributed at intervals exceeding 100 nm, on the other hand, the above-described effect on an increase in an area effective for the measurement of the properties, changes or the like of the substance cannot be brought about sufficiently.

The first fine-metal-particle thin film can be composed of at least one metal selected from the group consisting of gold, silver, copper, platinum and palladium.

A surface plasmon resonance sensor device according to a second aspect of the present invention has a core exposed portion disposed by exposing the peripheral surface of the core from a portion of the optical fiber.

A light incident to the optical fiber is introduced from one end thereof to the other end by the optical fiber in the surface plasmon resonance sensor device according to the second aspect. During the introduction, an evanescent wave is generated along the outer surface of the core in the core exposed portion. The evanescent wave thus generated resonantly excites surface plasmon on the outer surface of the thin metal film. As a result, the surface plasmon resonance sensor device according to the second aspect makes it possible to utilize the entire surface area of the core exposed portion as an area effective for the measurement of the properties, changes or the like of the substance along a direction of the incident light guided by the optical fiber, resulting in a marked improvement in the measurement accuracy.

According to the surface plasmon resonance sensor according to the second aspect, an electric field acts in a direction perpendicular to a direction of the incident light guided by the optical fiber so that the evanescent wave easily causes resonance excitation of surface plasmon. Excellent measurement accuracy can therefore be attained by the surface plasmon resonance sensor device of the second aspect.

The thin metal film may be formed by covering the entire surface of the core exposed portion, but it is preferred that the thin metal film has second microspheres which are formed integral with the core at the core exposed portion, and resonate an evanescent wave generated on the surface of the core while confining it in the second microspheres; and is formed by covering the second microspheres. When the second microspheres are formed integral with the core at the core exposed portion, the evanescent wave generated along the outer surface of the core is confined in the second microspheres and resonate by the repeated rotation. By the rotation of the evanescent wave in the second microspheres, the evanescent wave formed on the surface of the second microspheres resonantly excites surface plasmon on the outer surface of the thin metal film.

The evanescent wave rotates, for example, at a rate of $10^{10}$ times/ms for from 1 µs to 1 ms along the inner surface of the second microspheres. As a result, when the second microspheres each has a diameter of about 10 µm, an area effective for the measurement of the properties, changes or the like of the substance increases in proportion to the number of rotation of the evanescent wave in the second microspheres and becomes $10^7$ to $10^{10}$ times as much as the actual surface area of the second microsphere. It increases further in proportion to the number of the second microspheres. Accordingly, the surface plasmon resonance sensor device equipped with the core exposed portion, second microspheres formed integral with the core, and the thin metal film formed to cover the second microspheres enables more effective use of the surface area of the core exposed portion, whereby the measurement accuracy can be improved more greatly.

The thin metal film of the surface plasmon resonance sensor device according to the second aspect is preferably composed of a second covering layer having a thickness within a range of from 10 to 100 nm. When the thin metal film has a thickness less than 10 nm, it is sometimes difficult to form a uniform covering layer. When the thickness of the thin film exceeds 100 nm, on the other hand, the evanescent wave hardly penetrates through the covering layer, making it difficult to resonantly excite surface plasmon.

The second covering layer can be composed of at least one metal selected from the group consisting of gold, silver, copper and aluminum.

The thin metal film is more preferably composed of a second fine-metal-particle thin film in which fine metal particles having an average particle size of 50 nm or less are distributed uniformly at intervals of from 10 to 100 nm. When the thin metal film is the second fine-metal-particle thin film, localized surface plasmon resonance occurs owing to a similar principle to that of the above-described surface plasmon resonance so that an area effective for the measurement of the properties, changes or the like of the substance can be increased over that of the second covering layer and the measurement accuracy can be improved more greatly.

Occurrence of the localized surface plasmon resonance is presumed to be suppressed when the average particle size of the fine metal particles exceeds 50 nm. When the fine metal particles are distributed at intervals less than 10 nm, fine metal particles having an average particle size of 50 nm or less cannot be formed independently. When they are distributed at intervals exceeding 100 nm, on the other hand, the above-described effect on an increase in an area effective for the measurement of the properties, changes or the like of the substance cannot be brought about sufficiently.

The second fine-metal-particle thin film can be composed of, for example, at least one metal selected from the group consisting of gold, silver, copper, platinum and palladium.

DESCRIPTION OF THE PREFERRED EMBODIMENTS

Embodiments of the present invention will hereinafter be described more specifically with reference to accompanying drawings.

First, the constitution of a surface plasmon resonance sensor device 1a as one constitution example of the first aspect of the present invention will be described with reference to FIG. 1. The surface plasmon resonance sensor device 1a is equipped with an optical fiber 2, a microsphere 3 formed at the tip portion of the optical fiber 2 and a covering layer 4 made of a thin metal film formed on the surface of the microsphere 3.

The optical fiber 2 is composed of a light guiding core 5 which is a center portion of the fiber and a clad 6 encompassing the light conducting core 5 and it can transmit a light along the length direction of the light guiding core 5. The optical fiber 2 may be either a quartz fiber or a plastic fiber made of plastic such as polycarbonate.

The microsphere 3 is formed integral with the light conducting core 5 by removing the clad 6 from the tip portion of the optical fiber 2 to expose the light conducting core 6 and then, making the exposed portion of light conducting core 5 spherical. The microsphere 3 is large enough to confine therein the light guided by the light guiding core 5 and cause resonation. The diameter of the microsphere 3 varies, depending on the wavelength of a light to be guided, but it is, for example, several µm to several tens µm when a laser light is guided.

The covering layer 4 is a thin metal film formed to cover the entire surface of the microsphere 3 and it has a thickness ranging from 10 to 100 nm so that it can cause excitation of surface plasmon. The covering layer 4 is made of a single metal selected from the group consisting of gold, silver, copper and aluminum, or an alloy thereof.

A description will next be made of a manufacturing process of the surface plasmon resonance sensor device 1a of this Embodiment. First, a light conducting core 6 is exposed by removing a clad 6 from the tip portion of an optical fiber 2 and at the same time, the tip portion of a light guiding core 5 thus exposed is thinned. The tip portion is thinned by drawing under heat or etching with a chemical when the optical fiber 2 is a quartz fiber.

The etching can be carried out with an etchant containing HF or the like component capable of melting the light guiding core 5 and clad 6, for example, an etchant having the following composition: (40% aqueous ammonium fluoride solution):(50% HF):$H_2O$=X:1:1 (weight ratio, X represents a variable). The etching simultaneously removes the clad 6 and thins the light conducting core 5. An etching rate by the etchant varies, depending on the concentration of the 40% aqueous ammonium fluoride solution. The greater the value X, the lower the etching rate. The etching rate is 8 µm/hour when X=10.

When the optical fiber 2 is a plastic fiber, the above-described thinning is carried out by drawing under heat or melting in an organic solvent such as acetone or methyl acetate.

After the tip portion of the light conducting core 5 is thinned as described above, the thinned portion of the light conducting core 5 is exposed to a laser light such as $CO_2$ laser to melt the portion at a high energy density to make it spherical, whereby a microsphere 3 is formed. When the thinned portion of the light guiding core 5 is melted as described above, it becomes spherical by itself owing to a high surface tension of quartz or plastic so that the microsphere 3 having a high sphericity is formed.

The thinned portion of the light guiding core 5 may be melted by heating with a gas burner or the like, but heating by exposure to a laser light such as $CO_2$ laser is suited because the portion is very minute. The power density suited for exposure of quartz fiber to $CO_2$ laser is about 1000 W/cm², while that suited for exposure of plastic fiber is about 100 W/cm². The diameter of the microsphere 3 can be controlled by regulating the length of the thinned portion of the light conducting core 5.

A covering layer 4 is then formed over the entire surface of the microsphere 3 formed in the above-described manner. No particular limitation is imposed on the formation process of the covering layer 4 on the surface of the microsphere 3 and it can be formed in a manner known per se in the art such as vacuum deposition, sputtering, plating or the like. When the covering layer 4 is formed, for example, by vacuum deposition, a metal can be deposited on the surface of the microsphere 3 with a uniform thickness by carrying out vacuum deposition while rotating the microsphere 3. When the optical fiber 2 is a plastic fiber, a metal is deposited preferably at low temperature to prevent the damage of the plastic fiber.

Figure 2:
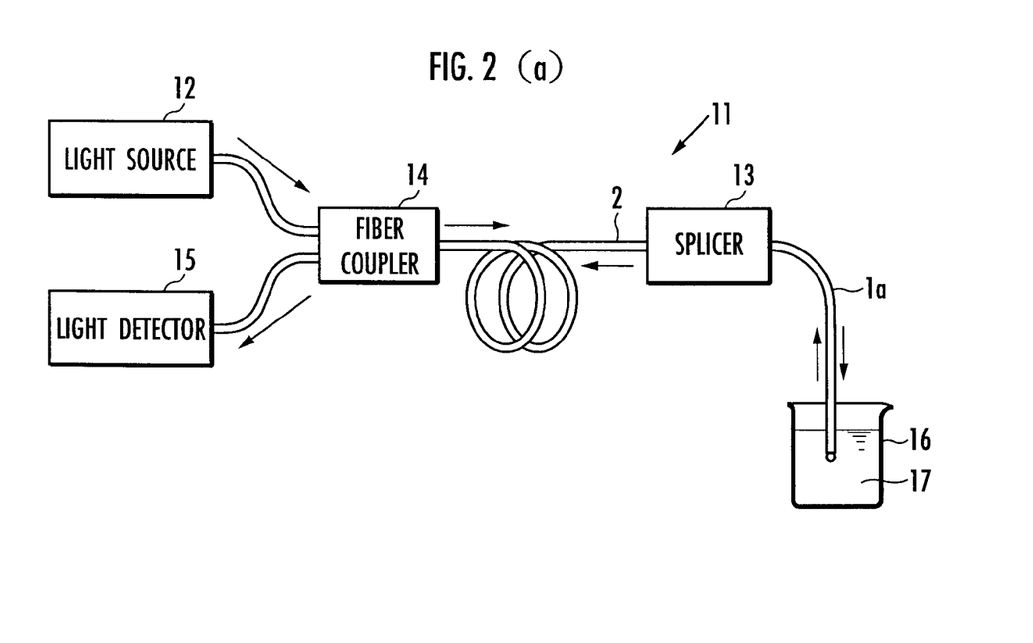
FIG. 2 is a system configuration diagram illustrating an example of a measuring apparatus using the surface plasmon resonance sensor device illustrated in FIG. 1.

The surface plasmon resonance sensor device 1a according to this Embodiment can be used, for example, a measuring apparatus 11 as illustrated in FIG. 2(a). The measuring apparatus 11 is equipped with a light source 12 connected to an end portion of the optical fiber 2 and the surface plasmon resonance sensor device 1a connected to the other end of the optical fiber 2 via a splicer 13. It is equipped further with a fiber coupler 14 disposed midway of the optical fiber 2 and a light detector 15 connected to the fiber coupler 14. The surface plasmon resonance sensor device 1a is brought into contact with a substance to be measured. When the substance to be measured is a solution 17 housed in a container 16, the device is dipped in the solution 17. The surface plasmon resonance sensor device 1a becomes disposable when it is connected to the optical fiber 2 via the splicer 13.

In the next place, the operation of the measuring apparatus 11 for detecting antigen-antibody reaction by using the surface plasmon resonance sensor device 1a of this Embodiment will be described with reference to FIGS. 2 to 4.

The optical fiber 2 is exposed to a laser light 18 with constant frequency or variable frequency such as titanium-sapphire laser light from the light source 12 of the measuring apparatus 11 as illustrated in FIG. 2. As illustrated in FIG. 3(a), the laser light 18 is then guided to the microsphere 3 at the tip portion of the optical fiber 2 via the light guiding core 5. Regulation of the wavelength of the laser light 18 by the light source 12 causes an optical confinement mode (WG (whispering-Gallery) mode) in which the laser light 18 confined in the microsphere 3 is rotated repeatedly and resonation is caused thereby. Appearance of the WG mode is followed by the generation of an evanescent wave (not illustrated) along the surface of the microsphere 3. The evanescent wave penetrating through the covering layer 4 made of a thin metal film resonantly excites surface plasmon on the outer surface of the covering layer 4. The laser light 18 rotates at a rate of about $10^9$ times/ms for from 1 to 10 ms along the inner surface of the microsphere 3 in the WG mode.

Figure 3:
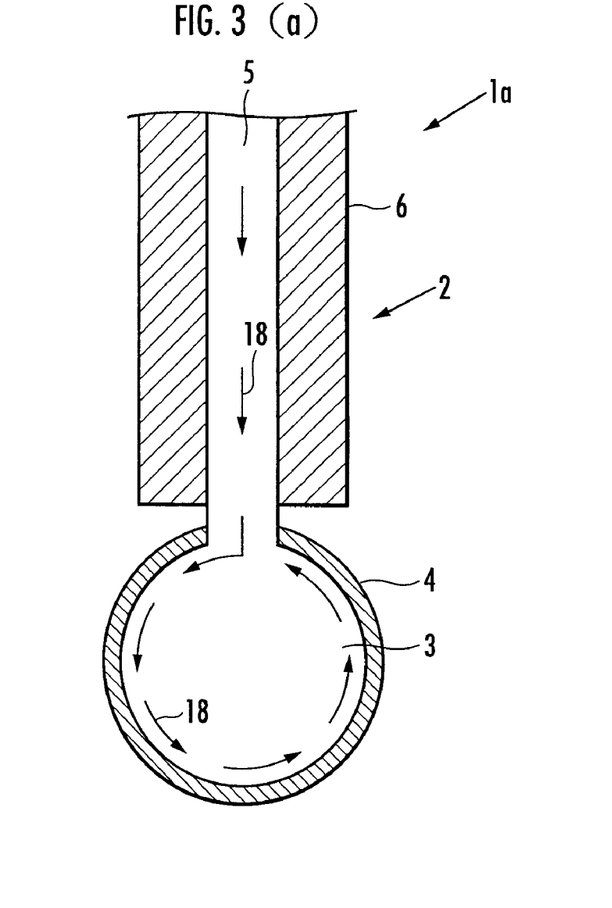
FIG. 3 is a schematic view illustrating the operation of the surface plasmon resonance sensor device illustrated in FIG. 1.
Figure 4:
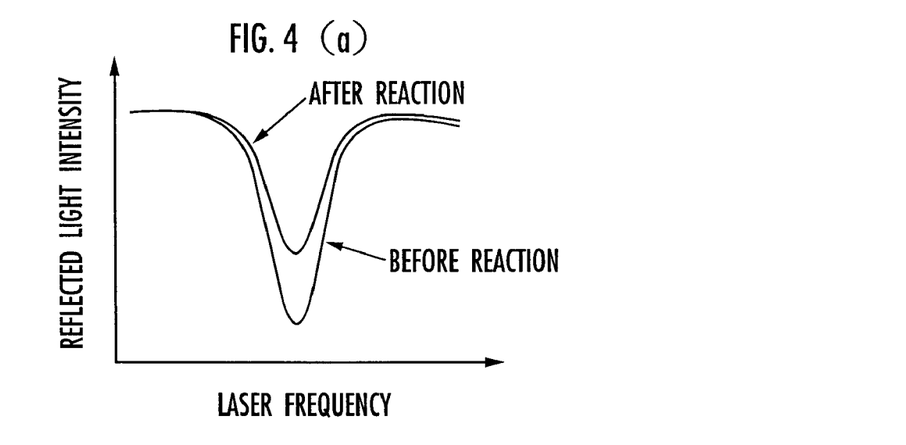
FIG. 4 is a graph showing the detection method of surface plasmon resonance in the surface plasmon resonance sensor device illustrated in FIG. 1.

As is apparent from an enlarged view of FIG. 3(b), a self-assembled monolayer 19 is formed on the surface of the covering layer 4 made of a thin metal film in order to avoid nonspecific adsorption and an antibody 20 is fixed as a ligand onto the self-assembled monolayer 19. An antigen 21 which specifically reacts with the antibody 20 is, on the other hand, incorporated as an acceptor in the solution 17 shown in FIG. 2.

When a specific antigen-antibody reaction occurs under such a state between the antigen 20 on the surface plasmon resonance sensor device 1a dipped in the solution 17 and the antigen 21 in the solution 17 and bonding (molecular adsorption) of the antigen 21 to the antibody 20 occurs, a dielectric constant (reflectance•refractive index) on the surface of the covering layer 4 made of a thin metal film changes from that before the reaction. It results in a change in resonance excitation conditions of surface plasmon on the surface of the covering layer 4 made of a thin metal film, leading to a change in the laser light 18 which is in the WG mode. A change of the laser light 18 is detected by a photodetector 15, whereby the antigen-antibody reaction can be detected.

When a variable single frequency laser, for example, is employed as the light source 12 of FIG. 2(a), use of, for example, a light-intensity detector as the light detector 15 makes it possible to detect a change in the laser light 18 from the reflected light of the laser light 18. In this case, as illustrated in FIG. 4(a), a large reduction in the reflected light intensity is observed at a specific frequency before the reaction (molecular adsorption), but a reduction in the reflected light intensity at a specific frequency becomes small owing to a change in the WG mode after the reaction (molecular adsorption).

When a wavelength variable ultrashort pulse laser having a pulse width of 1 ps is used as the light source 12 illustrated in FIG. 2(a), use of, for example, an ultrafast optical oscilloscope or streak camera as the light detector 15 enables detection of a change in the laser light 18 from the time until the reflected light intensity disappears. In this case, as illustrated in FIG. 4(b), it takes 1 ms or greater until the disappearance of the reflected light intensity before reaction (molecular adsorption), but owing to a change in the WG mode (disappearance of WG mode by plasmon resonation), the time drastically decreases even to about 1 ns after the reaction (molecular adsorption).

Moreover, a change in the laser light may be detected by detecting the emission intensity due to surface plasmon. In this case, as illustrated in FIG. 2(b), an adapter 22 is disposed at a position permitting detection of light emission due to surface plasmon, for example, a wall surface of the container 16 for the sample solution 17 and the light detector 15 is connected to the adapter 22 via an optical fiber 23.

As the light source 12 of FIG. 2(b), a variable single frequency laser can be used and in this case, a light detector 15 composed of, for example, a spectroscope and a light intensity detector can be used. As illustrated in FIG. 4(c), after the reaction (molecular adsorption), owing to the resonance between the evanescent light and surface plasmon, light emission peculiar to surface plasmon (for example, red light emission of about 630 nm in wavelength when fine metal particles are gold) is observed, though it is not observed before the reaction (molecular adsorption) owing to non-resonance.

The laser light 18 in the surface plasmon resonance sensor device 1a of this Embodiment rotates at a rate of about $10^9$ times/ms for from 1 to 10 ms along the inner surface of the microsphere 3 in the above-described WG mode so that an area effective for the detection of a change in the laser light 18 is from $10^9$ to $10^{10}$ times as much as the actual surface area of the microsphere 3. Accordingly, the surface plasmon resonance sensor device 1a enables marked increase in the measurement accuracy of a change in the laser light 18, that is, the antigen-antibody reaction.

The constitution of a surface plasmon resonance sensor device 1b as another constitution example of the first embodiment of the invention will next be described with reference to FIG. 5. The surface plasmon resonance sensor device 1b is equipped with an optical fiber 2, a microsphere 3 formed at the tip portion of the optical fiber 2, and a fine-metal-particle thin film 25 made of fine metal particles 24 formed on the surface of the microsphere 3.

Figure 1:
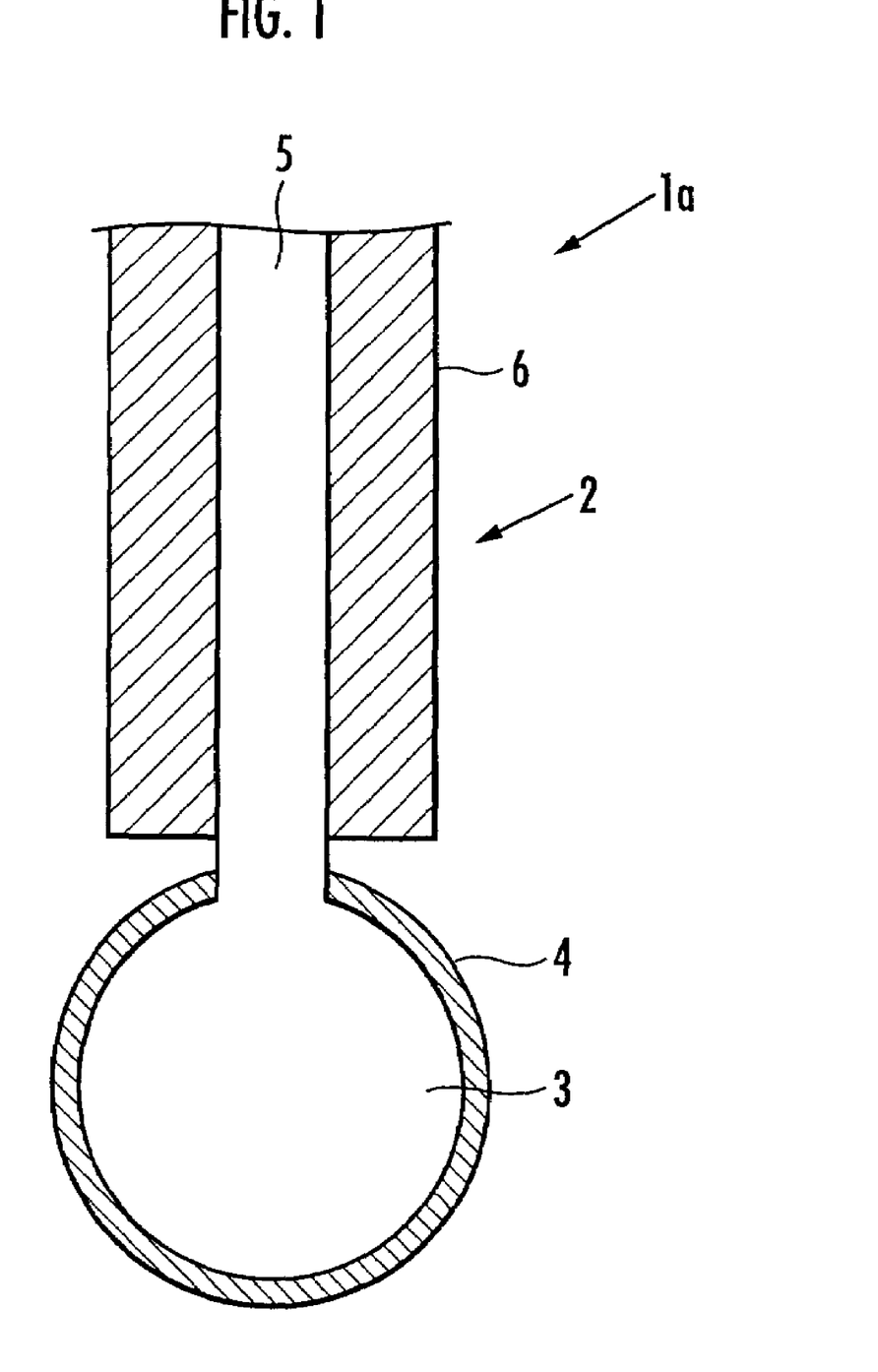
FIG. 1 is a schematic cross-sectional view illustrating a constitution example of a surface plasmon resonance sensor device according to the first aspect of the present invention.

The constitution of each of the optical fiber 2 and the microsphere 3 and formation process of the microsphere 3 are exactly the same as those of the surface plasmon resonance sensor device 1a illustrated in FIG. 1.

The fine metal particles 24 have an average particle size of 50 nm or less, are uniformly distributed on the surface of the microsphere at intervals of from 10 to 100 nm, and constitute the fine-metal-particle thin film 25. The fine metal particles 24 are made of a metal selected from the group consisting of gold, silver, copper, platinum and palladium, or an alloy thereof.

The fine metal particles 24 can be formed on the surface of the microsphere 3 by forming a thin film made of an oxide of a metal selected from the group consisting of gold, silver, copper, platinum and palladium or alloy thereof and then subjecting the resulting thin metal oxide film to reduction treatment with a hydrogen-containing gas.

Although no particular limitation is imposed on the formation process of the thin metal oxide film, vacuum film formation process is preferred. The vacuum film formation process may be any one of conventionally known DC sputtering such as RF reactive magnetron sputtering, vacuum deposition and ion plating. No particular limitation is imposed on a film forming apparatus.

The composition of the metal oxide when the film is formed is determined by an oxygen gas concentration to be used in the vacuum film formation process. When the oxygen concentration is high, a thin oxide film having a high oxygen content is available, while when the oxygen concentration is low, a thin film having a high metal content is available. The concentration of the oxygen gas or the introduction amount of the oxygen gas is an essential factor in determining the particle size of fine metal particles 24 constituting the fine-metal-particle thin film 25 after reduction with a hydrogen-containing gas so that it is preferred to determine the oxygen gas concentration and its introduction amount in advance in order to obtain fine metal particles 24 having a desired particle size. Although there is no particular limitation imposed on the thickness of the thin metal oxide film thus formed, it is usually from about 1 to 1000 nm.

The thin metal oxide film thus formed is then subjected to reduction treatment with a hydrogen-containing gas. As the hydrogen-containing gas, not only a gas containing only hydrogen but also a mixed gas with oxygen or a noble gas such as argon is usable.

The above-described reduction treatment may be wet reduction with an HF solution, but reduction treatment with hydrogen can be carried out safely under a low pressure by using a vacuum apparatus. In addition, the hydrogen reduction treatment performed under a low pressure by using a vacuum apparatus does not require heating so that it enables uniform treatment over a wide area and is therefore very effective when the optical fiber 2 is a plastic fiber. Reactive ion etching with the hydrogen-containing gas is therefore most preferred.

An amount of electricity used for the reactive ion etching is determined by the distance between electrodes and their size so that it is not particularly limited. Electricity of about 100 W is sufficient. The electricity to be input is set so as to prevent elimination of the metal by oxygen and to obtain a desired fine-metal-particle thin film 25.

The surface plasmon resonance sensor device 1b according to this Embodiment can be used in exactly the same manner as that of the surface plasmon resonance sensor device 1a illustrated in FIG. 1 except that localized surface plasmon is resonantly excited. By the surface plasmon resonance sensor device 1b according to this Embodiment, the localized surface plasmon is resonantly excited on each of the fine metal particles 24 constituting the fine-metal-particle thin film 25. Accordingly, compared with the covering layer 4 made of a thin metal film of the surface plasmon resonance sensor device 1a, the surface plasmon resonance sensor device 1b can increase an area effective for the measurement of the properties, changes or the like of the substance further, thereby greatly improving the measurement accuracy.

Figure 5:
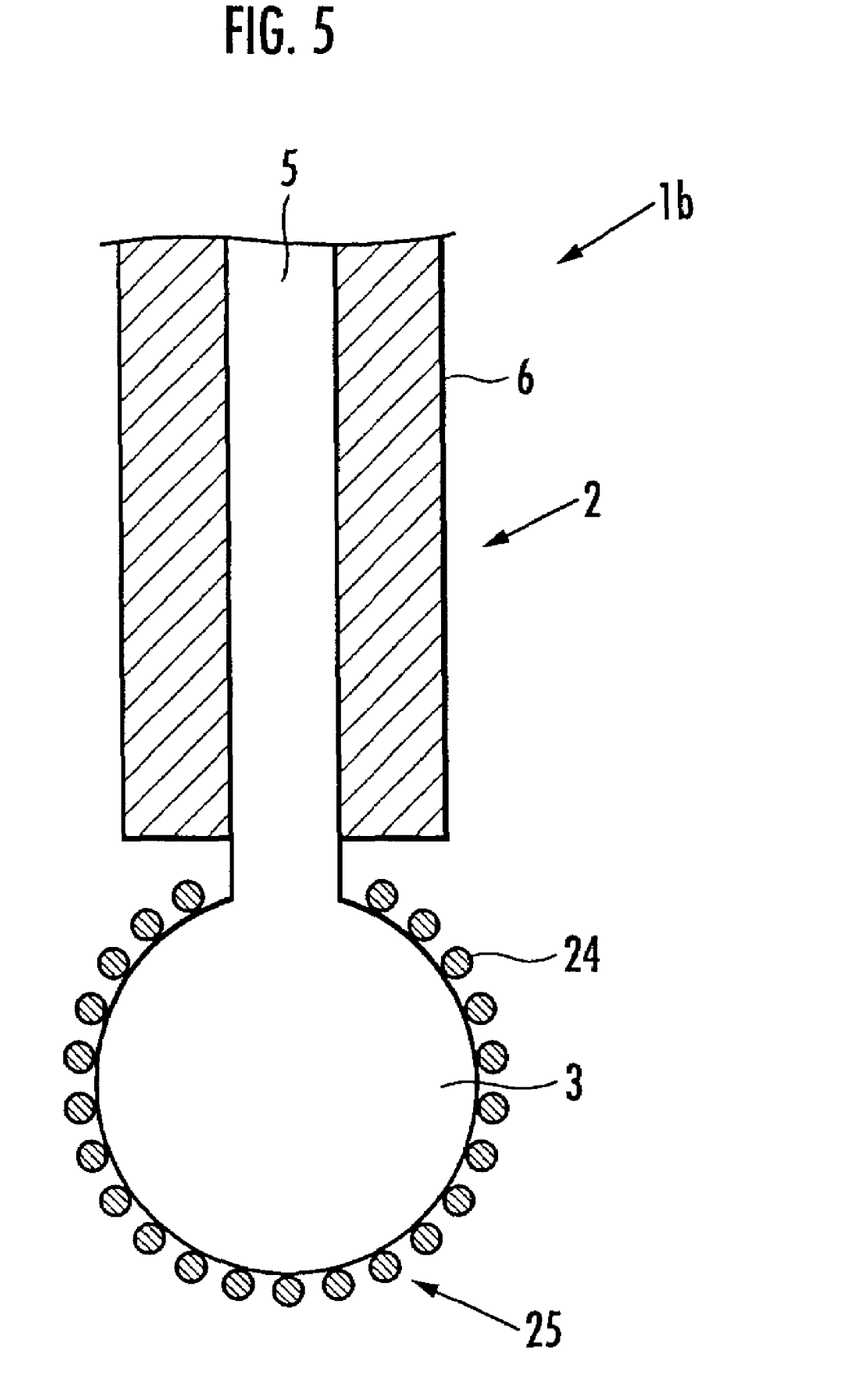
FIG. 5 is a schematic cross-sectional view illustrating another constitution example of the surface plasmon resonance sensor device according to the first aspect of the present invention.
Figure 6:
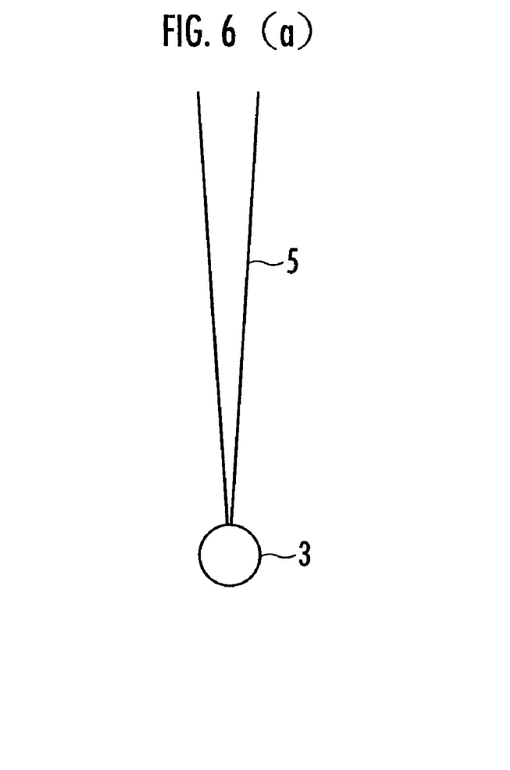
FIG. 6 is a schematic cross-sectional view illustrating a deformation example of the surface plasmon resonance sensor device according to the first aspect of the present invention.

In the above-described first embodiment, surface plasmon resonance sensor devices 1a and 1b equipped with a microsphere 3 at the tip portion of a linear light conducting core 5 as illustrated in FIGS. 1 and 5 were described, but the light conducting core 5 may have a tapered shape, that is, narrowed to point as illustrated in FIG. 6. The tapered shape can be formed, for example, by regulating the etching conditions or heat drawing conditions during thinning of the light conducting core 5. Formation of the tapered shape makes it possible to increase the light confinement effect in the microsphere further, thereby greatly improving the measurement accuracy.

When the light guiding core 5 has a tapered shape, the surface plasmon resonance sensor device 1a or 1b may be equipped with a single microsphere 3 at the tip portion of the tapered light guiding core as illustrated in FIG. 6(a), or may be equipped with a plurality of microspheres 3 on the side surface of the tapered light guiding core 5. A plurality of microspheres 3 can be disposed on the side surface of the tapered light conducting core 5 by bringing the microspheres 3, which have been prepared separately from the light conducting core, close to the side surface of the tip portion of the light conducting core 5 by using a piezo positioning apparatus. The microspheres 3 then naturally adhere to the side surface of the tip of the light conducting core 5 owing to van der Waals' force.

The covering layer 4 and fine-metal-particle thin film 25 are formed on the microsphere 3 illustrated in FIG. 6(a) and FIG. 6(b) in exactly the same manner as described above.

The constitution example of a surface plasmon resonance sensor device 31a as one constitution example of a second embodiment of the present invention will next be described with reference to FIG. 7. An optical fiber 32 constituting the surface plasmon resonance sensor device 31a is composed of a light conducting core 33 which is a center portion of the optical fiber and a clad 34 encompassing the light conducting core 33 and light can be transmitted along the length direction of the light conducting core 33. The surface plasmon resonance sensor device 31a has, in the midway of the optical fiber 32, a core exposed portion 33a from which the light conducting core 33 is exposed by peeling of a predetermined length of the clad 34 and a covering layer 35 made of a thin metal film formed on the surface of the core exposed portion 33a. The optical fiber 32 may be a quartz fiber or a plastic fiber made of plastic such as polycarbonate.

The covering layer 35 is a thin metal film formed to cover the entire surface of the core exposed portion 33a and has a thickness of from 10 to 100 nm enough for exciting surface plasmon. The covering layer 35 is made of a metal selected from the group consisting of gold, silver, copper and aluminum, or an alloy thereof.

The surface plasmon resonance sensor device 31a of this embodiment can be manufactured in the following manner. First, the core exposed portion 33a is formed by etching the clad 34 at a predetermined portion of the optical fiber 32 with a chemical or drawing it while melting under heat with a $CO_2$ laser.

The covering layer 35 is formed over the entire surface of the core exposed portion 33a formed as described above. The formation process of the covering layer 35 on the surface of the core exposed portion 33a is not particularly limited and can be formed in a manner known per se in the art such as vacuum deposition, sputtering or plating. When vacuum deposition is employed for the formation of the covering layer 35 and the optical fiber 32 is a plastic fiber, low-temperature deposition is preferred in order to prevent the plastic fiber from being damaged.

Figure 8:
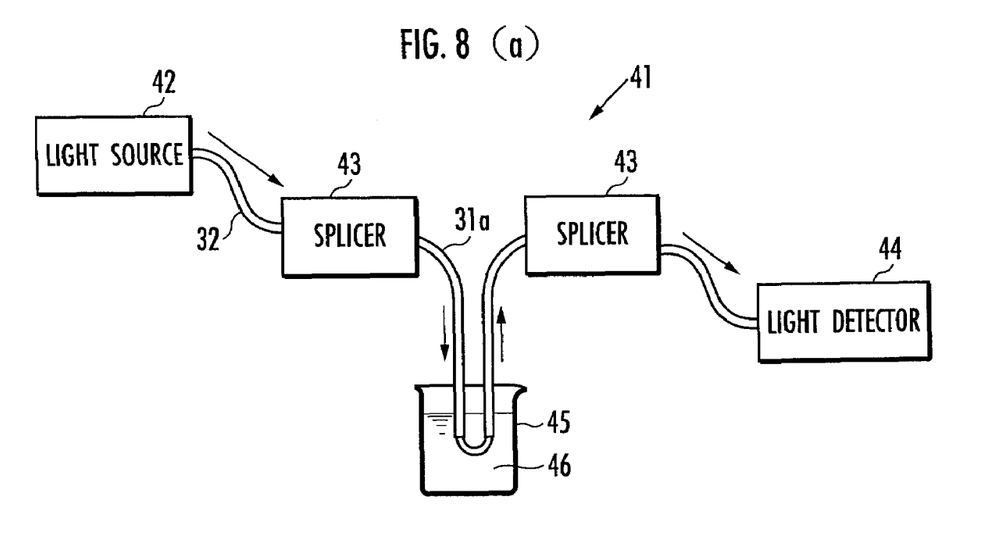
FIG. 8 is a system configuration diagram showing a constitution example of a measuring apparatus using the surface plasmon resonance sensor device illustrated in FIG. 7.

The surface plasmon resonance sensor device 31a according to this Embodiment can be used for a measuring apparatus 41 as illustrated, for example, in FIG. 8(a). The measuring apparatus 41 is equipped with a light source 42 connected to one end portion of the optical fiber 32, the surface plasmon resonance sensor device 31a connected between splicers 43 and 43 disposed in the midway of the optical fiber 32, and a light detector 44 connected to the other end portion of the optical fiber 32. The surface plasmon resonance sensor device 1a is brought into contact with a substance to be measured. When the substance to be measured is, for example, a solution 46 housed in a container 45, the device 31a is dipped in the solution 46. The surface plasmon resonance sensor device 31a is disposable when connected to the optical fiber 32 via the splicer 43.

In the next place, the operation of the measuring apparatus 11 will be described with reference to FIGS. 8 to 10 while taking, as an example, detection of antigen-antibody reaction by using the surface plasmon resonance sensor device 31a of this Embodiment.

In the measuring apparatus 41, the optical fiber 32 is exposed to a variable single frequency laser light 47 such as titanium-sapphire laser light from the light source 42 illustrated in FIG. 8. As illustrated in FIG. 9(a), the laser light 47 is then guided from one end of the optical fiber 32 to the other end via the light guiding core 33. When the wavelength of the laser light 47 is regulated by the light source 42, an evanescent wave (not illustrated) is generated along the outer surface of the core exposed portion 33a. The evanescent wave penetrates through the covering layer 35 made of a thin metal film and resonantly excites surface plasmon on the outer surface of the covering layer 35 made of a thin metal film. In the surface plasmon resonance sensor device 31a, an electric field acts in a direction perpendicular to the laser light 47 guided along the length direction of the light guiding core 33, which facilitates resonant excitation of surface plasmon on the outer surface of the covering layer 35.

Figure 9:
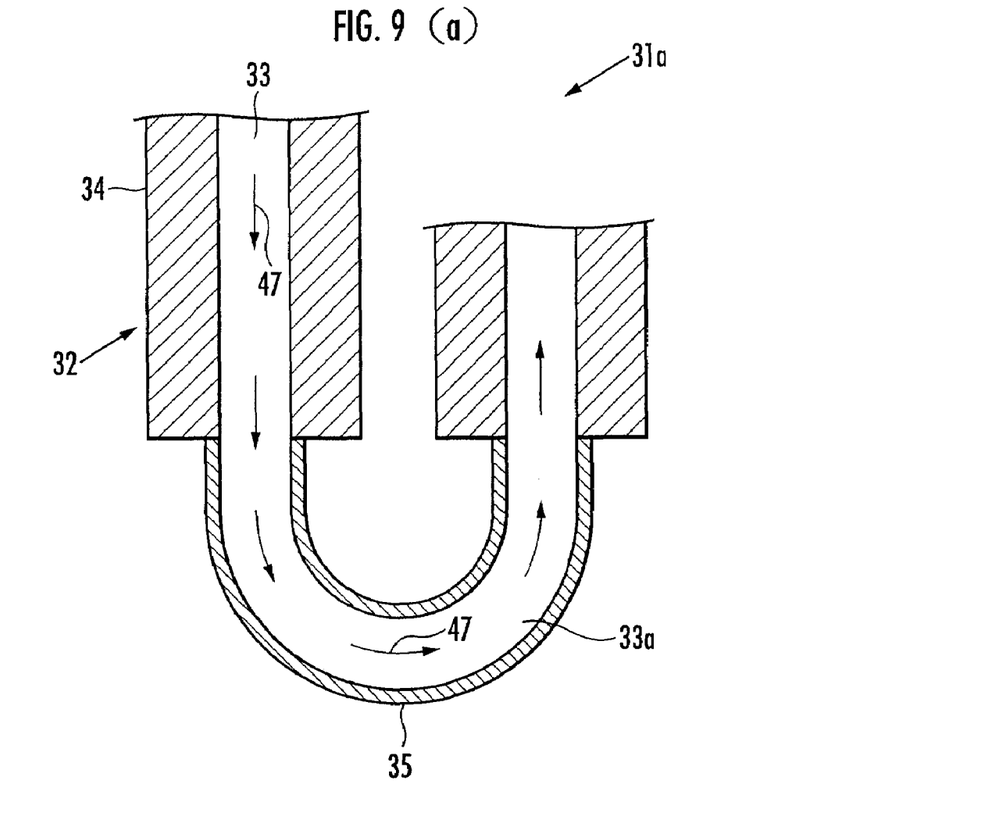
FIG. 9 is a schematic view illustrating the operation of the surface plasmon resonance sensor device illustrated in FIG. 7.
Figure 10:
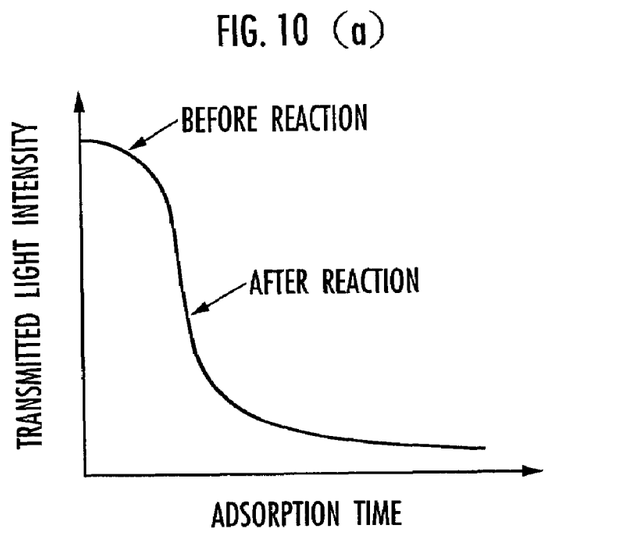
FIG. 10 is a graph showing the detection method of surface plasmon resonance in the surface plasmon resonance sensor device illustrated in FIG. 7.

As is apparent from an enlarged view of FIG. 9(b), a self-assembled monolayer 48 is formed on the surface of the covering layer 35 made of a thin metal film in order to avoid nonspecific adsorption and an antibody 49 is fixed as a ligand onto the self-assembled monolayer 48. An antigen 50 which specifically reacts with the antibody 49 is, on the other hand, incorporated as an acceptor in the solution 46 shown in FIG. 8.

When a specific antigen-antibody reaction occurs under such a state between the antibody 49 on the surface plasmon resonance sensor device 31a dipped in the solution 46 and the antigen 50 in the solution 46 and bonding (molecular adsorption) of the antigen 50 to the antibody 49 occurs, a dielectric constant (reflectance•refractive index) on the surface of the covering layer 35 made of a thin metal film changes from that before the reaction. It results in a change in resonance excitation conditions of surface plasmon on the surface of the covering layer 35 made of a thin metal film, leading to a change in the laser light 47. The change of the laser light 47 is detected by a photodetector 44, whereby the antigen-antibody reaction can be detected.

When a variable single frequency laser, for example, is employed as the light source 42 of FIG. 8(a), use of, for example, a light-intensity detector as the light detector 44 makes it possible to detect a change in the laser light 47 from the transmitted light intensity of the laser light 47. In this case, as illustrated in FIG. 10(a), a drastic reduction in the transmitted light intensity occurs after the reaction (molecular adsorption).

A change in the laser light 47 may be detected indirectly by detecting the emission intensity of light from surface plasmon. In this case, as illustrated in FIG. 8(b), an adapter 51 is disposed at a position where light emission from surface plasmon can be detected, for example, wall surface of the container 45 of the sample solution 46 and the light detector 44 is connected to the adapter 51 via an optical fiber 52.

As the light source 42 of FIG. 8(b), a variable single frequency laser can be used and in this case, a light detector 44 composed of, for example, a spectroscope and a light intensity detector can be used. As illustrated in FIG. 10(b), owing to the resonance between the evanescent light and surface plasmon after the reaction (molecular adsorption), light emission specific to surface plasmon (for example, red light emission with a wavelength of about 630 nm when fine metal particles are made of gold) is observed, though it is not observed before the reaction (molecular adsorption) owing to non-resonance.

In the surface plasmon resonance sensor device 31a, all of the surface area of the core exposed portion 33a formed along a guiding direction of the laser light 47 can be used for measuring a change in the laser light 47. In addition, an electric field acts in a direction perpendicular to the guiding direction of the laser light 47, which facilitates resonance excitation of surface plasmon on the outer surface of the covering layer 35. Accordingly, a change in the laser light 47, in other words, the antigen-antibody reaction can be measured with markedly improved measurement accuracy.

Figure 11:
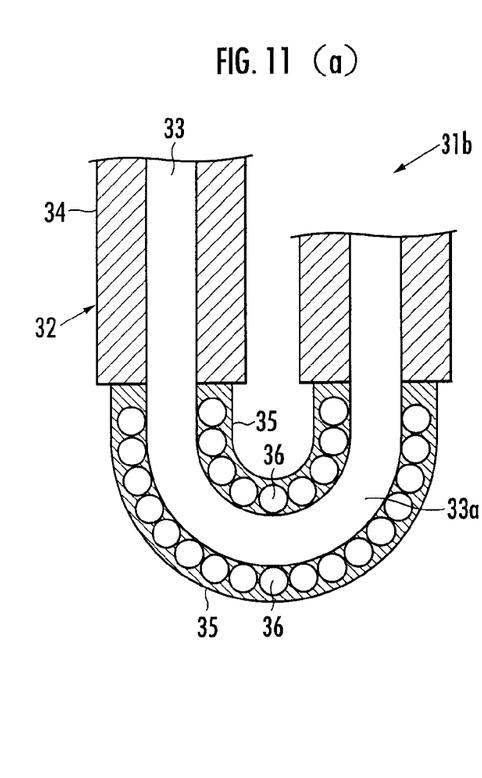
FIG. 11 is a schematic cross-sectional view illustrating another constitution example of the surface plasmon resonance sensor device according to the second aspect of the present invention.

The constitution of surface plasmon resonance sensor devices 31b to 31d as other constitution examples of the second embodiment will next be described with reference to FIG. 11.

Figure 7:
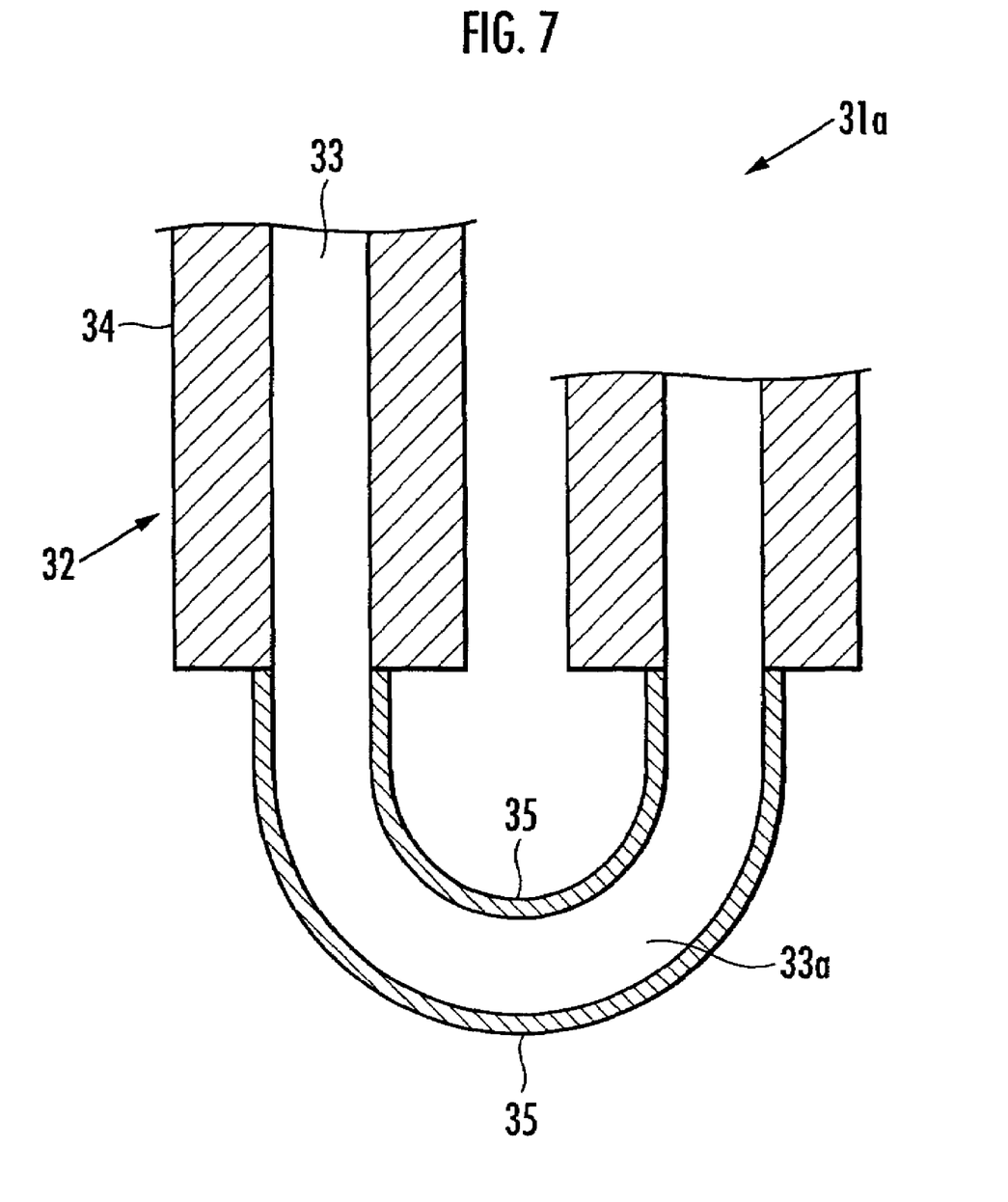
FIG. 7 is a schematic cross-sectional view illustrating a constitution example of a surface plasmon resonance sensor device according to a second aspect of the present invention.

In the surface plasmon resonance sensor device 31b illustrated in FIG. 11(a), a plurality of microspheres 36 made of a similar material to that of the light conducting core 33 are attached to the core exposed portion 33a formed in exactly the same manner as that of the surface plasmon resonance sensor device 31a illustrated in FIG. 7 and the device is equipped with a covering layer 35 made of a thin metal film formed on the surfaces of the core exposed portion 33a and the microspheres 36.

Commercially available quartz or polystyrene latex microspheres are used as the microspheres 36. In order to obtain microspheres 36 of a desired size, first the tip portion of the light conducting core 33 is thinned simultaneously with the removal of the clad 34 from the tip portion of the optical fiber 32. The above-described thinning is carried out by drawing under heat or etching with a chemical when the optical fiber 32 is a quartz fiber.

The etching can be carried out with an etchant containing HF or the like component capable of melting the light guiding core 33 and clad 34, for example, an etchant having the following composition: (40% aqueous ammonium fluoride solution):(50% HF):$H_2O$=X:1:1 (weight ratio, X representing a variable). The etching simultaneously removes the clad 34 and thins the light conducting core 33. An etching rate of the etchant varies, depending on the concentration of the 40% aqueous ammonium fluoride solution. The greater the value X, the lower the etching rate. The etching rate is 8 μm/hour when X=10.

When the optical fiber 32 is a plastic fiber, it is thinned by drawing under heat or melting in an organic solvent such as acetone or methyl acetate.

After the tip portion of the light conducting core 33 is thinned as described above, the thinned portion of the light conducting core 33 is exposed to a laser light of a $CO_2$ laser or the like to melt the potion at a high energy density to make it spherical. When the thinned portion of the light guiding core 33 is melted as described above, it becomes spherical by itself owing to a high surface tension of quartz or plastic so that the microspheres 36 having a high sphericity are formed.

The thinned portion of the light guiding core 33 may be melted by heating with a gas burner or the like, but heating by exposure to a laser light of a $CO_2$ laser or the like is suited because the portion is very minute. When exposure to $CO_2$ laser is employed, a power density of about 1000 W/cm$^2$ is suited for quartz fiber, while that of about 100 W/cm$^2$ is suited for plastic fiber. The diameter of the microspheres 36 is, for example, about 10 µm and it can be controlled by regulating the length of the thinned portion of the light conducting core 33.

By bringing the microspheres 36, which have been formed in the above-described manner, close to the surface of the core exposed portion 33a by using a piezo positioning apparatus, it naturally adheres to the surface of the core exposed portion 33a owing to van der Waals' force. The covering layer can be formed on the core exposed portion 33a to cover the microspheres 36 therewith in a similar manner to that employed for the surface plasmon resonance sensor device 31a illustrated in FIG. 7.

The surface plasmon resonance sensor device 31b having the above-described constitution can be used in exactly the same manner as the surface plasmon resonance sensor device 31a illustrated in FIG. 7. According to the surface plasmon resonance sensor device 31b of this Embodiment, an evanescent wave (not illustrated) is generated along the surface of the core exposed portion 33a by regulating the wavelength of the laser light 47 irradiated from the light source 42 to the optical fiber 32 illustrated in FIG. 8.

The evanescent wave combines with an optical resonance mode of the microspheres 36, leading to occurrence of an optical confinement mode (WG (whispering-Gallery) mode) in which repeated rotation of a light confined in the microspheres and resonation caused thereby appears. When the WG mode appears, the evanescent wave of the microspheres 36 in the WG mode resonantly excites surface plasmon on the outer surface of the covering layer 35. In the above-described WG mode, the laser light 18 rotates at a rate of about $10^{10}$ times/ms for from 1 µm to 1 ms along the inner surface of the microspheres 36.

As a result, an area effective for detecting a change in the laser light 17 becomes $10^7$ to $10^{10}$ times as much as the actual surface area per microsphere 36 and it increases further in proportion to the number of the microspheres 36. Accordingly, the surface plasmon resonance sensor device 31b enables more effective use of the surface area of the core exposed portion 33b, thereby remarkably improving the measurement accuracy.

The surface plasmon resonance sensor device 31c illustrated in FIG. 11(b) has a fine-metal-particle thin film 38 made of fine metal particles 37 on the surface of the core exposed portion 33a formed in exactly the same manner as that of the surface plasmon resonance sensor device 31a illustrated in FIG. 7.

A surface plasmon resonance sensor device 31d illustrated in FIG. 11(c) is equipped with microspheres (for example, quartz microspheres) 36 formed in exactly the same manner as those of the surface plasmon resonance sensor device 31b illustrated in FIG. 11(a) on the surface of the core exposed portion 33a formed in exactly the same manner as that of the surface plasmon resonance sensor device 31a illustrated in FIG. 7; and a fine-metal-particle thin film 38 made of fine metal particles 37 on the surface of the microspheres 36.

The fine metal particles 37 have an average particle size of 50 nm or less. They are uniformly distributed at intervals of from 10 to 100 nm on the surface of the core exposed portion 33a or the surfaces of the microspheres 36 and constitute the fine-metal-particle thin film 38. The fine metal particles 37 are made of a metal selected from the group consisting of gold, silver, copper, platinum and palladium, or an alloy thereof.

The fine metal particles 37 can be formed by forming a thin film made of an oxide of a metal selected from the group consisting of gold, silver, copper, platinum and palladium or alloy thereof and then subjecting the resulting thin metal oxide film to reduction treatment with a hydrogen-containing gas. Although no particular limitation is imposed on the preparation process of the thin metal oxide film, a vacuum film formation process is preferred. The vacuum film formation process may be any one of conventionally known DC sputtering such as RF reactive magnetron•sputtering, vacuum deposition and ion plating. No particular limitation is imposed on a film forming apparatus.

The composition of the metal oxide when the film is formed is determined by an oxygen gas concentration to be used in the vacuum film formation process. When the oxygen concentration is high, a thin oxide film having a high oxygen content is available, while when the oxygen concentration is low, a thin film having a high metal content is available. The concentration of the oxygen gas or the introduction amount of the oxygen gas is an essential factor in determining the particle size of fine metal particles 37 constituting the fine-metal-particle thin film 38 after reduction with a hydrogen-containing gas so that it is preferred to determine the oxygen gas concentration and its introduction amount in advance in order to obtain fine metal particles 24 having a desired particle size. Although there is no particular limitation imposed on the thickness of the thin metal oxide film thus formed, it is usually from about 1 to 1000 nm.

The thin metal oxide film thus formed is then subjected to reduction treatment with a hydrogen-containing gas. As the hydrogen-containing gas, not only a gas containing only hydrogen but also a mixed gas with oxygen or a noble gas such as argon is usable.

The above-described reduction treatment may be wet reduction with an HF solution, but reduction treatment with hydrogen can be carried out safely under a low pressure by using a vacuum apparatus. In addition, the hydrogen reduction treatment performed under a low pressure by using a vacuum apparatus does not require heating so that it enables uniform treatment over a wide area and is therefore very effective when the optical fiber 32 is a plastic fiber. Reactive ion etching with the hydrogen-containing gas is therefore most preferred.

An amount of electricity used for the reactive ion etching is determined by the distance between electrodes and the magnitude of electricity so that it is not particularly limited. Electricity of about 100 W is adequate. The electricity to be input is set so as to prevent elimination of the metal by oxygen and to obtain a desired fine-metal-particle thin film 38.

The surface plasmon resonance sensor device 31d according to this Embodiment can be used in exactly the same manner as that of the surface plasmon resonance sensor device 31a illustrated in FIG. 7 except that localized surface plasmon is resonantly excited. By the surface plasmon resonance sensor device 31d according to this Embodiment, the localized surface plasmon is resonantly excited on each of the fine metal particles 37 constituting the fine-metal-particle thin film 38. Accordingly, compared with the covering layer 35 made of a thin metal film of the surface plasmon resonance sensor device 31a illustrated in FIG. 7, the surface plasmon resonance sensor device 31d can increase an area effective for the measurement of the laser light 47, thereby greatly improving the measurement accuracy.

What is claimed is:
1. A surface plasmon resonance sensor device, comprising:
   an optical fiber for introducing light incident from one end thereof to the other end,
   a core exposed portion formed to expose the core of the optical fiber, and
   a thin metal film formed on the core exposed portion and capable of exciting surface plasmon, wherein the core exposed portion is a first microsphere disposed at the other end portion of the optical fiber for confining a light guided by the optical fiber in the microsphere to cause resonation, and the thin metal film is formed on the surface of the first microsphere.

2. A surface plasmon resonance sensor device according to claim 1, wherein the optical fiber is a quartz fiber.

3. A surface plasmon resonance sensor device according to claim 1, wherein the optical fiber is a plastic fiber.

4. A surface plasmon resonance sensor device according to claim 1, wherein the thin metal film is made of a first covering layer formed to cover the entire surface of the first microsphere and having a thickness ranging from 10 to 100 nm.

5. A surface plasmon resonance sensor device according to claim 4, wherein the first covering layer is made of at least one metal selected from the group consisting of gold, silver, copper and aluminum.

6. A surface plasmon resonance sensor device according to claim 1, wherein the thin metal film is made of a first fine-metal-particle thin film in which fine metal particles having an average particle size of 50 nm or less have been distributed uniformly at intervals of from 10 to 100 nm.

7. A surface plasmon resonance sensor device according to claim 6, wherein the first fine-metal-particle thin film is made of at least one metal selected from the group consisting of gold, silver, copper, platinum and palladium.

8. A surface plasmon resonance sensor device, comprising:
   an optical fiber for introducing light incident from one end thereof to the other end,
   a core exposed portion formed to expose the core of the optical fiber, and
   a thin metal film formed on the core exposed portion and capable of exciting surface plasmon,
   wherein the core exposed portion is disposed to expose the peripheral surface of the core in the midway of the optical fiber, and
   wherein the core exposed portion is equipped with a second microsphere which is formed integral with the core and confines, in the second microsphere, an evanescent wave generated on the surface of the core to cause resonation; and the thin metal film is formed to cover therewith the second microsphere.

9. A surface plasmon resonance sensor device according to claim 8, wherein the thin metal film is composed of a second covering layer having a thickness ranging from 10 to 100 nm.

10. A surface plasmon resonance sensor device according to claim 9, wherein the second covering layer is made of at least one metal selected from the group consisting of gold, silver, copper and aluminum.

11. A surface plasmon resonance sensor device according to claim 8, wherein the thin metal film is made of a second fine-metal-particle thin film in which fine metal particles having an average particle size of 50 nm or less are distributed uniformly at intervals of from 10 to 100 nm.

12. A surface plasmon resonance sensor device according to claim 11, wherein the second fine-metal-particle thin film is made of at least one metal selected from the group consisting of gold, silver, copper, platinum and palladium.

13. A surface plasmon resonance sensor device according to claim 8, wherein the optical fiber is a quartz fiber.

14. A surface plasmon resonance sensor device according to claim 8, wherein the optical fiber is a plastic fiber.

* * * * *